(12) United States Patent
Yoon et al.

(10) Patent No.: US 9,265,517 B2
(45) Date of Patent: Feb. 23, 2016

(54) SURGICAL DISC REMOVAL TOOL

(71) Applicant: GLOBUS MEDICAL, INC., Audubon, PA (US)

(72) Inventors: Samuel Yoon, Wyndmoor, PA (US); Ryan Agard, Royersford, PA (US); Jason Pastor, Philadelphia, PA (US); Sean Suh, Jamesburg, NJ (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

(21) Appl. No.: 14/683,320

(22) Filed: Apr. 10, 2015

(65) Prior Publication Data
US 2015/0209070 A1    Jul. 30, 2015

Related U.S. Application Data

(63) Continuation of application No. 14/319,895, filed on Jun. 30, 2014, now Pat. No. 9,028,517, which is a continuation of application No. 14/057,116, filed on Oct. 18, 2013, now Pat. No. 8,801,738, which is a continuation of application No. 13/362,440, filed on Jan. 31, 2012, now Pat. No. 8,585,726.

(51) Int. Cl.
| | |
|---|---|
| *A61B 17/32* | (2006.01) |
| *A61B 17/3207* | (2006.01) |
| *A61B 17/22* | (2006.01) |
| *A61B 17/00* | (2006.01) |

(52) U.S. Cl.
CPC ......... *A61B 17/320016* (2013.01); *A61B 17/22* (2013.01); *A61B 17/32002* (2013.01); *A61B 17/320725* (2013.01); *A61B 17/320758* (2013.01); *A61B 17/320783* (2013.01); *A61B 17/320708* (2013.01); *A61B 2017/00261* (2013.01); *A61B 2017/00685* (2013.01); *A61B 2017/320064* (2013.01); *A61B 2017/320733* (2013.01)

(58) Field of Classification Search
CPC ................ A61B 17/32002; A61B 17/320725; A61B 17/320783; A61B 17/22; A61B 17/320016; A61B 2017/00261; A61B 2017/00685; A61B 2017/320733; A61B 17/320758; A61B 17/320708; A61B 2017/320064
See application file for complete search history.

(56) References Cited

U.S. PATENT DOCUMENTS

| | | | |
|---|---|---|---|
| 5,047,040 A | 9/1991 | Simpson et al. | |
| 5,217,479 A | 6/1993 | Shuler | |
| 5,709,698 A | 1/1998 | Adams et al. | |
| 5,782,795 A | 7/1998 | Bays | |
| 6,042,593 A | 3/2000 | Storz et al. | |
| 6,183,433 B1 | 2/2001 | Bays | |
| 6,217,598 B1 | 4/2001 | Berman et al. | |
| 6,620,180 B1 | 9/2003 | Bays et al. | |
| 2011/0054507 A1* | 3/2011 | Batten ................ | A61B 17/1615 606/170 |
| 2011/0270294 A1 | 11/2011 | Rubin | |
| 2012/0053484 A1 | 3/2012 | Parks | |
| 2012/0101513 A1 | 4/2012 | Shadeck et al. | |
| 2012/0172905 A1 | 7/2012 | Lee Shee et al. | |

\* cited by examiner

*Primary Examiner* — Ashley Fishback

(57) ABSTRACT

The disclosure provides a tissue removal device including customizable tips. The tissue removal device may include an outer shaft and a threaded shaft. One aspect of disclosure may include a shaft cutting tool that emerges from the end of the outer shaft. Another aspect of the disclosure may include a flexible cutting blade extending from the threaded shaft. Threaded shaft may be driven by a driving mechanism in order to provide an auger-like suction mechanism to facilitate the transfer of removed tissue to a collection chamber that is coupled to the outer shaft and the threaded shaft.

14 Claims, 7 Drawing Sheets

SURGICAL DISC REMOVAL TOOL

CROSS REFERENCE TO RELATED APPLICATIONS

This patent application is a continuation of U.S. patent application Ser. No. 14/319,895, filed on Jun. 30, 2014, which is a continuation application of U.S. patent application Ser. No. 14/057,116 filed on Oct. 18, 2013, now U.S. Pat. No. 8,801,738, which is a continuation application of U.S. Ser. No. 13/362,440 filed on Jan. 31, 2012, now U.S. Pat. No. 8,585,726, the contents of these applications being incorporated herein in their entireties for all purposes.

BACKGROUND OF THE PRESENT DISCLOSURE

1. Field of the Present Disclosure

The present disclosure is generally directed to a surgical device. More specifically, the disclosure may be directed to a surgical device that facilitates the removal of tissue.

2. Related Art

A spine comprises a series of small bones referred to as vertebrae. Spinal discs are fixed in place between each pair of vertebrae and function like a pad or cushion to prevent the vertebrae from grinding against each other and permit the spine to be flexible. A variety of scenarios may exist where damage to one or more of these spinal discs may occur including, but not limited to, injury and illness. Severe, even debilitating, pain can result from such damage.

Surgical procedures exist that attempt to alleviate the pain that accompanies such damage. At least one of these procedures may involve the removal of at least a portion of tissue associated with a spinal disc. Many conventional devices currently exist on the market for facilitating the removal of tissue associated with a spinal disc. However, each conventional device suffers from one or more drawbacks.

Conventional devices exist which suffer from the problem of being purely manual. Such manual devices require the use of human muscle, which fatigues, to perform the procedure. Additionally, such manual devices require significantly more time to complete the procedure as opposed to devices which have one or more powered, or otherwise mechanical, components.

However, merely providing for a powered device that facilitates removal of tissue associated with a spinal disc does not completely remedy the drawbacks of conventional devices. Many existing powered disc removal devices require expensive capital equipment to power the device. Additionally, surgeons are reluctant to use powered devices designed for removal of at least a portion of tissue associated with a spinal disc because the devices are overpowered or lack proper safety measures.

Furthermore, conventional devices have drawbacks in their ability to remove tissue associated with the spinal disc that has been severed. Typically, existing devices, whether manual or powered, rely solely on suction manufactured by generated airflow in order to remove tissue associated with a spinal disc that has been cut. Such an approach includes various drawbacks, including requiring a device capable of generating the suction. This requires at least the extra capital expense of purchasing a device capable of generating the requisite suction.

Accordingly, there is a need for device that improves a surgeon's ability to remove at least a portion of tissue associated with a spinal disc without relying solely on suction generated by airflow.

SUMMARY OF THE PRESENT DISCLOSURE

The present disclosure meets the foregoing need of improving a surgeon's ability to remove at least a portion of tissue associated with a spinal disc without relying solely on suction generated by airflow.

Accordingly, one aspect of the present disclosure describes a tissue removal device. The tissue removal device may include an outer shaft and a threaded shaft. The tissue removal device may include a customizable tip. The customizable tip serves to increase the versatility of the tissue removal device by providing a choice of a specific shaft, cutting instrument, or both in order to customize the tissue removal device.

At least one aspect of the disclosure may include a shaft cutting tool that emerges from an end of an outer shaft. Another aspect of the disclosure may include a flexible cutting blade extending from a threaded shaft. Threaded shaft may be driven by a driving mechanism in order to provide an auger-like suction mechanism to facilitate the transfer of removed tissue to a collection chamber that is coupled to the outer shaft and threaded shaft.

According to another aspect of the present disclosure the collection chamber includes at least a partial enclosure. At least a portion of this enclosure includes transparent material that allows for the inspection of the inside of the collection chamber. Additionally, the collection chamber may comprise a pluggable hole and/or a pluggable port that may aid in providing versatility to a surgeon utilizing the tissue removal device.

According to another aspect of the present disclosure, the flexible cutting blade may be expanded or contracted. Expanding or contracting the flexible cutting blade may increase or decrease the cutting diameter of the flexible cutting blade. In accordance with this feature, one aspect of the disclosure may include a window on the handle of the tissue removal device. The window may provide a visual indicator as to the height of the flexible cutting blade.

Additional features, advantages, and aspects of the present disclosure may be set forth or apparent from consideration of the following detailed description, drawings, and claims. Moreover, it is to be understood that both the foregoing summary of the present disclosure and the following detailed description are exemplary and intended to provide further explanation without limiting the scope of the present disclosure as claimed.

BRIEF DESCRIPTION OF THE DRAWINGS

The accompanying drawings, which are included to provide a further understanding of the present disclosure, are incorporated in and constitute a part of this specification, illustrate aspects of the present disclosure and together with the detailed description serve to explain the principles of the present disclosure. No attempt is made to show structural details of the present disclosure in more detail than may be necessary for a fundamental understanding of the present disclosure and the various ways in which it may be practiced. In the drawings.

DETAILED DESCRIPTION OF THE PRESENT DISCLOSURE

Figure 1:
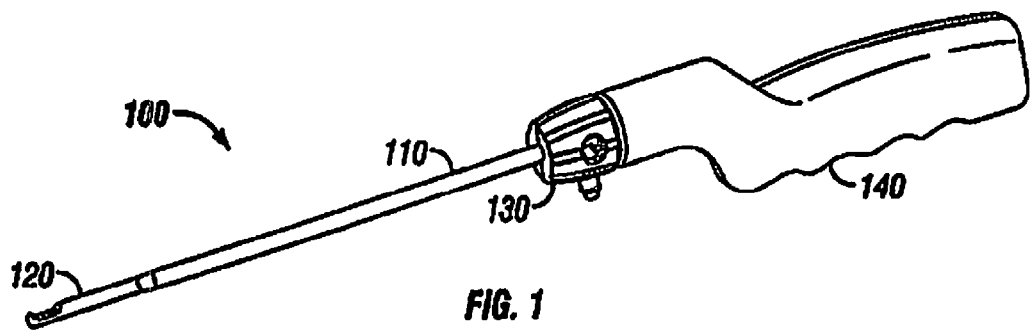
FIG. 1 shows a tissue removal device, according to an aspect of the present disclosure.

The aspects of the present disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the present disclosure. The examples used herein are intended merely to facilitate an understanding of ways in which the present disclosure may be practiced and to further enable those of skill in the art to practice the aspects of the present disclosure. Accordingly, the examples and aspects herein should not be construed as limiting the scope of the present disclosure, which is defined solely by the appended claims and applicable law. Moreover, it is noted that like reference numerals represent similar parts throughout the several views of the drawings.

The present disclosure is generally directed to a surgical device. More specifically, the disclosure may be directed to a device, used by a surgeon, to facilitate the removal of tissue.

The word "surgeon", as used in this disclosure, means any person that uses the disclosure to either sever tissue or attempt to sever tissue. Such a person may be educated, certified, and trained to perform surgical procedures involving the removal of tissue. Such a person may also be a lay person with no experience in the surgical field. In addition, such a person may have a skill-set, education, and/or knowledge base which falls somewhere between a person who is educated, certified, and trained to perform surgical procedures and a lay person.

The word "tissue", as used in this disclosure, means any tissue associated with a spinal disc. Such tissue can comprise many forms, including tissue from the inside of the disc referred to as the nucleus, tissue from the outside of the disc referred to as the annulus, or tissue associated with any other portion of a spinal disc. Such tissue may also comprise any tissue that resides in the surrounding area of the spine which is, or may reasonably cause, discomfort that may be associated with a spinal disc. Such tissue may also comprise any tissue that may be found in a carbon based life form.

FIG. 1 shows a tissue removal device according to an aspect of the present disclosure. The tissue removal device 100 may include an outer shaft 110, a customizable tip 120, collection chamber 130, and handle 140. The outer shaft 110 extends from the customizable tip 120 to the collection chamber 130. In at least one aspect of the present disclosure, outer shaft 110 may enclose a threaded shaft (not shown). Handle 140 provides a member that a surgeon may use for holding, controlling, and/or directing the tissue removal device. The handle 140 may include a variety of grips that may facilitate use and control of the tissue removal device 100, including, e.g., rubber, plastic, wood, metal, etc.

Customizable tip 120 provides tissue removal device 100 with increased versatility. Customizable tip 120 facilitates the altering of the tip of tissue removal device 100, as well as, the accompanying cutting instrument (discussed herein below). The customizable tip 120 may comprise either a tip, a cutting instrument, or both. When the customizable tip 120 does not include a cutting instrument, it is an aspect of the present disclosure that the corresponding outer shaft 110 or threaded shaft may be fitted with a cutting instrument as needed. The customizable tip 120 may be provided in, e.g., a sealed and sterilized packaging. The customizable tip 120 may be disposable.

Customizable tip 120 may be coupled to tissue removal device 100 in a plurality of different ways. For example, the customizable tip 120 and the outer shaft 110 may be constructed as a single, unibody structure that connects to the collection chamber 130 through a connector (discussed herein below).

The customizable tip 120 may be a detachable component that is designed to be coupled to the outer shaft 110, which extends to the collection chamber through a connector.

The customizable tip 120 may be designed to extend from the threaded shaft as either a unibody structure or as a detachable component. It is readily understood by one of ordinary skill in the art that the present disclosure need not be so limited. The customizable tip 120 may be coupled to the tissue removal device 100 in any manner which provides for the tip and/or cutting instrument of the tissue removal device 100 to be customized.

Figure 2A:
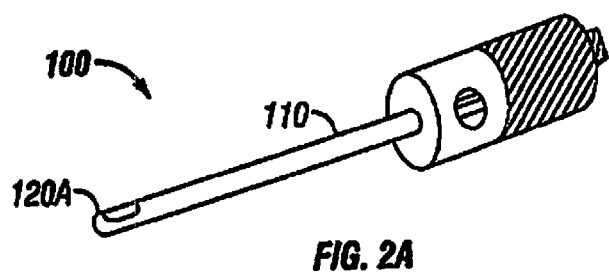
FIG. 2A shows an example of a customizable tip.
Figure 2B:
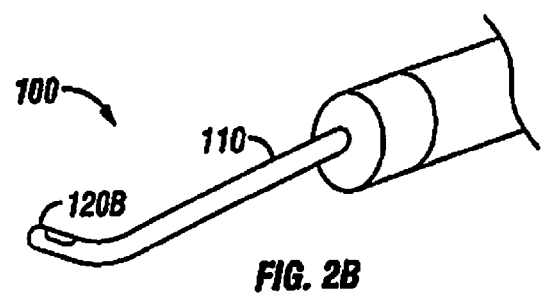
FIG. 2B shows another example of a customizable tip, which includes an angled portion.
Figure 2C:
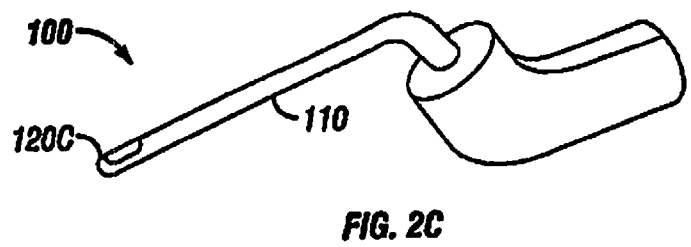
FIG. 2C shows yet another example of a customizable tip, which includes an angled portion.

FIGS. 2A, 2B, and 2C provide non-limiting examples of a variety of customizable tips 120 (120A, 120B, 120C, respectively).

FIG. 2A shows a customizable tip 120A that is similar to the customizable tip disclosed in FIG. 1, 120. As seen, the customizable tip 120A may include a substantially straight customizable tip. The customizable tip 120A is accompanied by the straight outer shaft 110. The outer shaft 110 may be mounted to (or through) the collection chamber. As seen in FIG. 2A, the collection chamber may have a housing that is substantially cylindrical in shape and the outer shaft 110 may be affixed to (or through) an end of the collection chamber.

FIG. 2B shows a customizable tip 120B that may be curved, angled, or otherwise formed, shaped or molded. The customizable tip 120B may be accompanied by the straight outer shaft 110 and the collection chamber.

FIG. 2C shows a customizable tip 120C that may be fitted to the tissue removal device 100, where the customizable tip 120C is accompanied by a curved outer shaft 110. The curved outer shaft 110 may be mounted to (or through) a curved collection chamber. As seen in FIG. 2C, an aspect of the disclosure contemplates that instead of the outer tip of outer shaft 110 being angled, the portion of outer shaft 110 which extends from the collection chamber 130, or other portion of tissue removal device 100 may be curved, angled, or otherwise shaped, formed, or molded in a manner which facilitates a more versatile tissue removal device 100.

Figure 3:
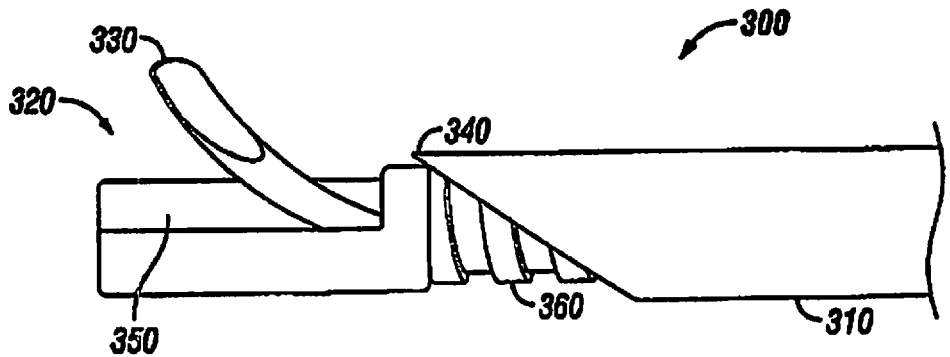
FIG. 3 shows an example of a cutting portion of a tissue removal device, according to an aspect of the present disclosure.
Figure 10:
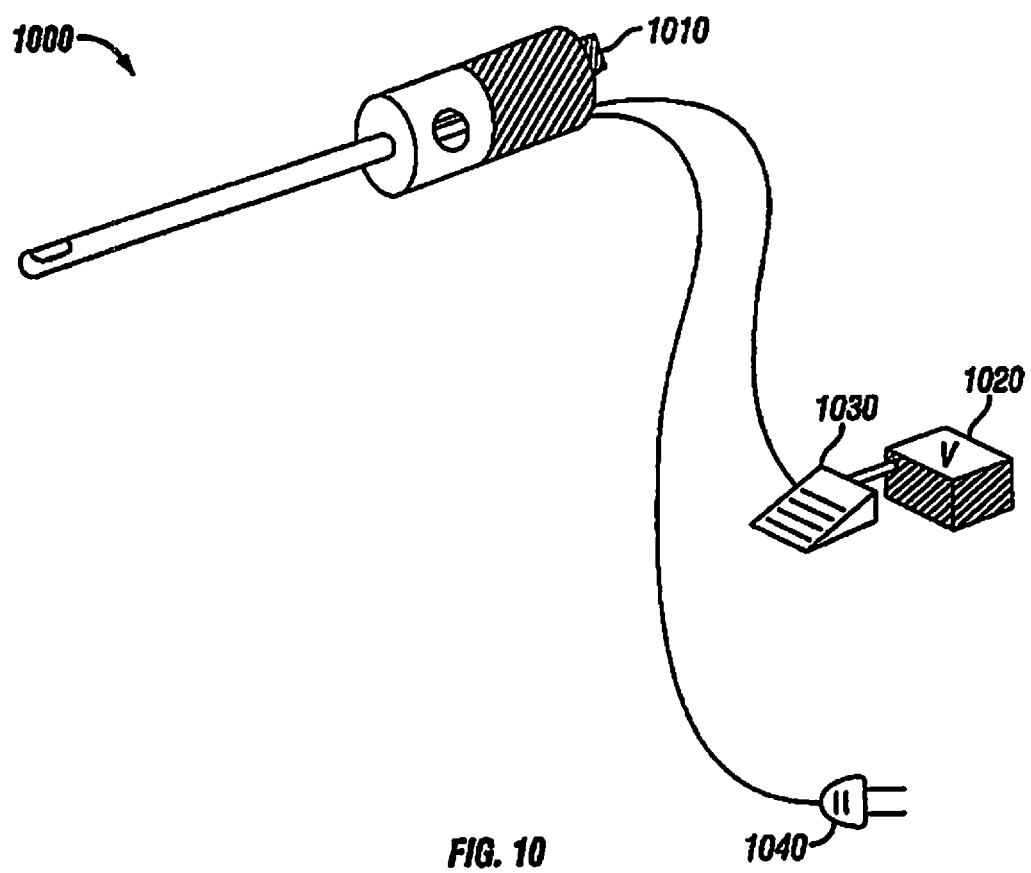
FIG. 10 shows a tissue removal system, including power connections and a tissue removal device.

FIG. 3 shows a cutting portion 300 of a tissue removal device (e.g., the tissue removal device 100, shown in FIG. 1, or the tissue removal device in the tissue removal system 1000, shown in FIG. 10). According to an aspect of the present disclosure, the tissue removal device (e.g., the tissue removal device 100, shown in FIG. 1) may include the cutting portion 300 in lieu of, or in addition to the customizable tip 120 and outer shaft 110. In the former case, the cutting portion 300 may be provided in the outer shaft 110 and configured to adjustably extend into an open section in the customizable tip 120, so as to contact and sever a tissue material. In the latter case, the cutting portion 300 may replace the customizable tip 120.

The cutting portion 300 includes a customizable tip 320 and an outer shaft 310. The cutting portion 300 may further include a shaft cutting tool 340. The customizable tip 320 may include a flexible cutting blade 330, a sample retriever 350, and a threaded shaft 360. The outer shaft 310 may encapsulate and guide the threaded shaft 360, as well as the customizable tip 320. The shaft cutting tool 340 may be integrally formed with the outer shaft 310, or it may be provided as a separate element that is connected to the outer shaft 310. The shaft cutting tool 340 and flexible cutting blade 330 provide two cutting mechanisms that are capable of severing material, including, e.g., tissue connected to a carbon based life form, thereby making tissue available for removal. The cutting blade 330 may be expanded or contracted to increase or decrease a cutting diameter. The adjustable cutting blade 330 allows a surgeon to accommodate varying patient anatomy and pathology. The severed tissue may be retrieved by the sample retriever 350. The threaded shaft 360, enclosed within the outer shaft 310, mechanically operates as a conveyor to move, convey, or transfer the severed tissue from the surgical site through the outer shaft 310 and into the collection chamber 130. The outer shaft 310 may be sized such that the tissue remains in contact with the threaded shaft 360 to prevent cutter portion 300 from jamming.

Figure 4:
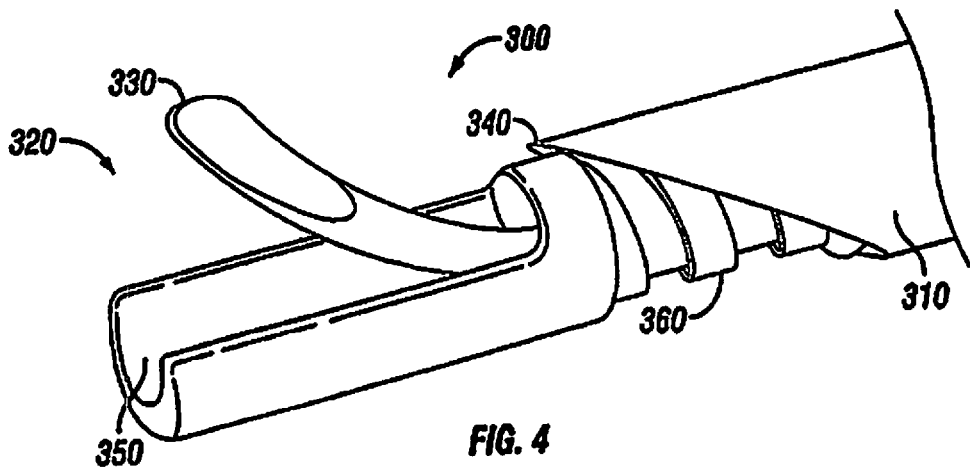
FIG. 4 shows an enlarged, perspective view of the cutting portion shown in FIG. 3.

FIG. 4 shows a perspective, enlarged view of the cutting portion 300. This enlarged view of the cutting portion 300 more clearly accents the features of the cutting portion 300 at the tip end of the device. As seen in FIG. 4, the shaft cutting tool 340 is configured to emerge from the end of the outer shaft 310, so that it may facilitate tissue severing. Shaft cutting tool 340 may function independently, or in conjunction with the flexible cutting blade 330, to provide a surgeon with improved control and precision in removing a desired portion of tissue.

In the cutting portion 300, the flexible cutting blade 330 may extend from an end of the threaded shaft 360, or another member (not shown) extending from the collection chamber 130. When extending from the end of the threaded shaft 360, flexible cutting blade 330 may revolve at the same rotational velocity as the threaded shaft 360 when driven by, e.g., a motor (not shown).

Flexible cutting blade 330 provides a surgeon with the advantage of accommodating carbon based life forms of varying anatomies and pathologies. This advantage is achievable by the configuration of the flexible cutting blade 330, which may be expandable and/or contractible for optimal positioning and severing of tissue. In this regard the cutting blade 330 may be extracted from the threaded shaft 360 to increase the cutting diameter or may be retracted into the threaded shaft 360 to reduce the cutting diameter. In other words, the cutting portion 300 may provide a surgeon with the ability to contract flexible cutting blade 330 in order to decrease its cutting diameter. Alternatively, or in combination, the cutting portion 300 may provide a surgeon with the ability to expand the length of flexible cutting blade 330 in order to increase its cutting diameter. Flexible cutting blade 330 may be made from, e.g., nitinol. However, it will be readily understood by one of ordinary skill in the art that the flexible cutting blade 330 of the present disclosure need not be so limited. The flexible cutting blade 330 of the present disclosure may be made of any material capable of severing tissue and providing the flexibility described herein, including, but not limited to, any metal, alloy, plastic, etc.

An aspect of the present disclosure provides a feature to accommodate precise use of flexible cutting blade 330. It will be readily understood by one of ordinary skill in the art that cutting portion 300 may be connected (directly or indirectly) to a handle similar to handle 140 of the tissue removal device 100. Accordingly, an aspect of the present disclosure provides that a window (not shown) may be cut into or formed in the handle 140. The window may provide a surgeon with a visual indicator as to the height of flexible cutting blade 330, thereby ensuring that the surgeon may more precisely use tissue removal device 100.

Additionally, the sample retriever 350 may function to retrieve the tissue that is removed by shaft cutting tool 340 and/or flexible cutting blade 330. This could happen in a plurality of ways. For example, either the shaft cutting tool 340 or the flexible cutting blade 330 may independently sever the tissue. This approach results in the tissue detaching from the carbon based life form and being collected in the sample retriever 350. Alternatively, or in combination, for example, the threaded shaft 360 may be mechanically retracted, thereby pulling the sample retriever 350 towards the collection chamber 130 through the outer shaft 310 which pushes flexible cutting blade 330 toward the sample retriever 350, thereby severing the tissue, and effectively trapping the tissue in the sample retriever 350. However, it will be readily understood by one of ordinary skill in the art that the present disclosure need not be so limited. As a result, other ways to sever and collect tissue for depositing in the collection chamber which fall within the spirit and scope of the invention may be realized in accordance with the present disclosure.

After tissue is severed and retrieved by sample retriever 350, threaded shaft 360 works as a conveyor to convey, move, or transfer the tissue away from the surgical site, through outer shaft 310, and into the collection chamber 130. Threaded shaft 360, enclosed by outer shaft 310, may be driven by a driving mechanism including, e.g., a motor (not shown). When driven by a driving mechanism, the threaded shaft 360 provides an alternative to conventional suction mechanisms that are generated purely based upon airflow. This alternative sample collection mechanism includes, e.g., the motor to revolve or rotate the threaded shaft 360 in order to provide an auger-like suction capability. The motor may be powered by a battery (see FIG. 10). Utilizing a motor to implement an auger-like suction mechanism provides the advantage of being able to power the tissue removal device 100 with batteries, while avoiding high cost capital equipment to drive a device that generates suction based on airflow. When flexible cutting blade 330 extends from the end of the threaded shaft 360, flexible cutting blade 330 may revolve at the same rotational velocity as threaded shaft 360 when driven by a motor (not shown). It is noted that the auger-like suction capability described herein above is driven by a motor. However, it would be readily understood by one of ordinary skill in the art that the auger-like suction capability of the present disclosure need not be so limited. As such, the auger-like suction capability of the present disclosure may be driven by other means, e.g., manually.

Figure 5:
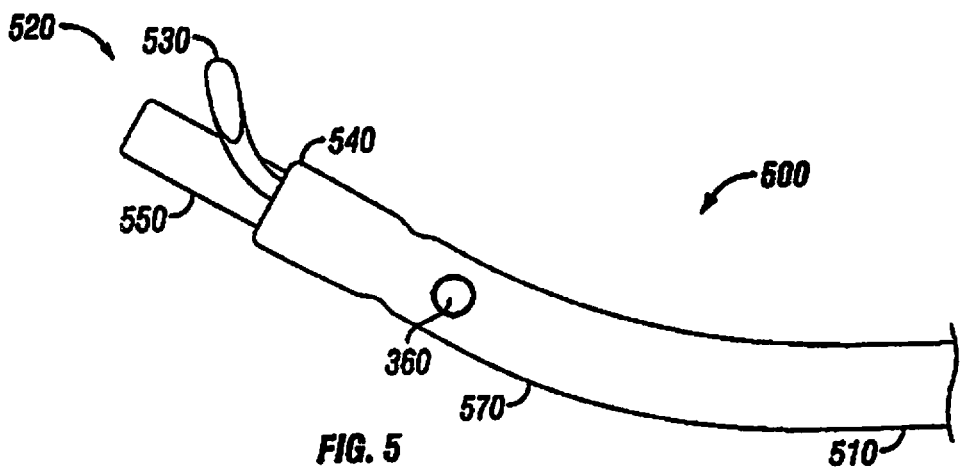
FIG. 5 shows another example of a cutting portion of a tissue removal device, according to an aspect of the present disclosure.

FIG. 5 shows another example of a cutting portion 500 of a tissue removal device (e.g., the tissue removal device 100, shown in FIG. 1, or the tissue removal device in the tissue removal system 1000, shown in FIG. 10). According to an aspect of the present disclosure, the tissue removal device (e.g., the tissue removal device 100, shown in FIG. 1) may include the cutting portion 500 in lieu of, or in addition to the customizable tip 120 and outer shaft 100. In the former case, the cutting portion 500 may be provided in the outer shaft 110 and configured to adjustably extend into an open section in the customizable tip 120, so as to contact and sever a tissue material. In the latter case, the cutting portion 500 may replace the customizable tip 120.

The cutting portion 500 may include a customizable tip 520, an angled shaft 570, and an outer shaft 510. The customizable tip 520 may include a flexible cutting blade 530, a shaft cutting tool 540, a sample retriever 550, and a threaded shaft 360. Angled shaft 570 may provide the cutting portion 500 with the capability of reaching a surgical site that is unreachable by, for example, the straight outer shaft 110 structure seen in FIG. 1.

The angled shaft 570 and the outer shaft 510 may be formed as a single unibody structure. Alternatively, the angled shaft 570 and outer shaft 510 may be formed from two or more parts, including, e.g., detachable components that may be coupled to each other.

Figure 6A:
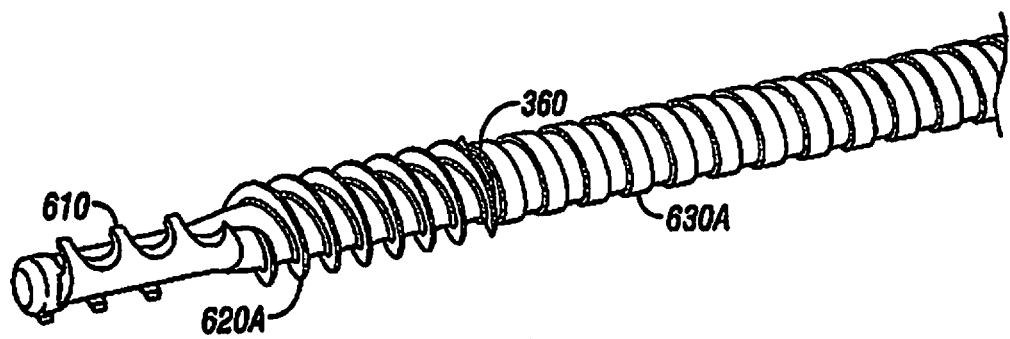
FIG. 6A shows a perspective view of a cutter shaft that may be used in another example of a cutting portion of a tissue removal device, according to an aspect of the present disclosure.

FIG. 6A shows an example of a cutter shaft that may be included within an outer shaft of a tissue removal device, such as, e.g., tissue removal device 100. A motor (not shown) may be provided to turn or revolve the threaded shaft 360, thereby providing an auger-like suction capability. Since cutter 610 extends from the end of threaded shaft 360, cutter 610 will rotate at the same rotational velocity as threaded shaft 360. The cutter may include one or more helical portions to move tissue to the next part of the threaded shaft 360, a sharp threaded section 620A. Threaded shaft 360 may comprise a plurality of sections, wherein each section provides a different threading. The threaded shaft 360 may be formed from a single piece of material, or from multiple pieces of materials.

As seen, the threaded shaft 360 may comprise the sharp threaded section 620A followed by a flatter threaded section 630A. The sharp threaded section 620A may provide better gripping and quicker transportation of particles. Once the tissue samples pass the threaded section 620A, the flatter threaded section 630A may be configured to receive the tissue samples and convey, move, or transfer the tissue samples to the collection chamber 130. The threaded section 620A may include, e.g., helical fins, to provide better gripping and quicker transportation of tissue samples from the cutter 610. The flatter threaded section 630A may include, e.g., helical patterns, to convey tissue from the threaded section 620A to, e.g., the collection chamber 130. It is noted that the threaded shaft 360 may include, for example, a single lead thread auger, a double lead thread auger (as shown in FIG. 6A), a triple lead thread auger, or a greater number of lead thread augers.

Figure 6B:
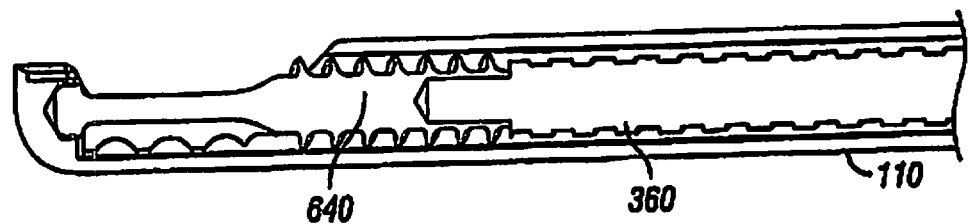
FIG. 6B shows a cross-section or cut-away view of another example of a cutting portion of a tissue removal device, including the cutter shaft of FIG. 6A.

FIG. 6B shows a cut-away view that illustrates a threaded shaft 360 (shown in FIG. 6A) being retracted in the outer shaft 110 towards the collection chamber 130. The threaded shaft 360 may engage the outer shaft 110 via an engagement mechanism 640, which may include, e.g., threading, grooves, channels, or the like. The motor drives the threaded shaft 360, forcing the threaded shaft 360 to revolve (or rotate) and interact with the engagement mechanism 640 to transport tissue from the cutter 610 to the collection chamber 130. In this manner, threaded shaft 360 functions to convey, move, or transfer tissue samples from the surgical site to the collection chamber 130. The outer shaft 110 may be sized so that a tissue sample will remain in contact with the threaded shaft 360 to prevent the auger-like suction mechanism from jamming.

Figure 6C:
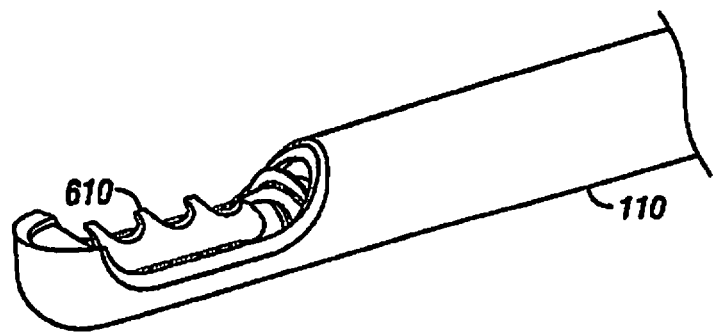
FIG. 6C shows a perspective view of the cutting portion of FIG. 6B.

FIG. 6C shows a perspective view of the cutter 610 residing within the outer shaft 110. Cutter 610 revolves at the same rotational velocity as its accompanying threaded shaft. When cutter 610 is revolving, and comes into contact with tissue, it severs one or more portions of tissue—i.e., one or more tissue samples—which are then conveyed, moved, or transferred to collection chamber 130 via the auger-like suction capability of, e.g., helical fin structure of the cutter 610, the sharp threaded section 620A, and the flatter threaded section 630A.

Figure 7A:
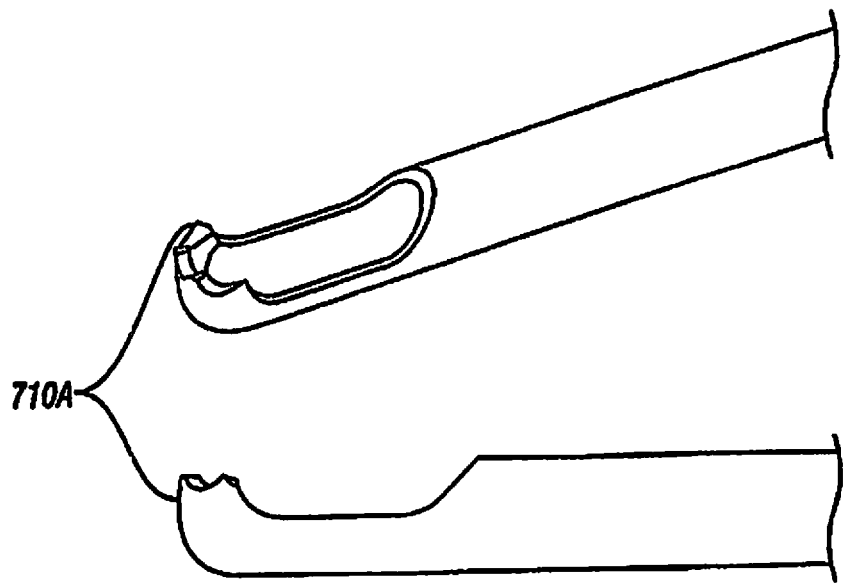
FIG. 7A shows a perspective view and a side view of a customized tip comprising a serrated curette tip shaft.
Figure 7B:
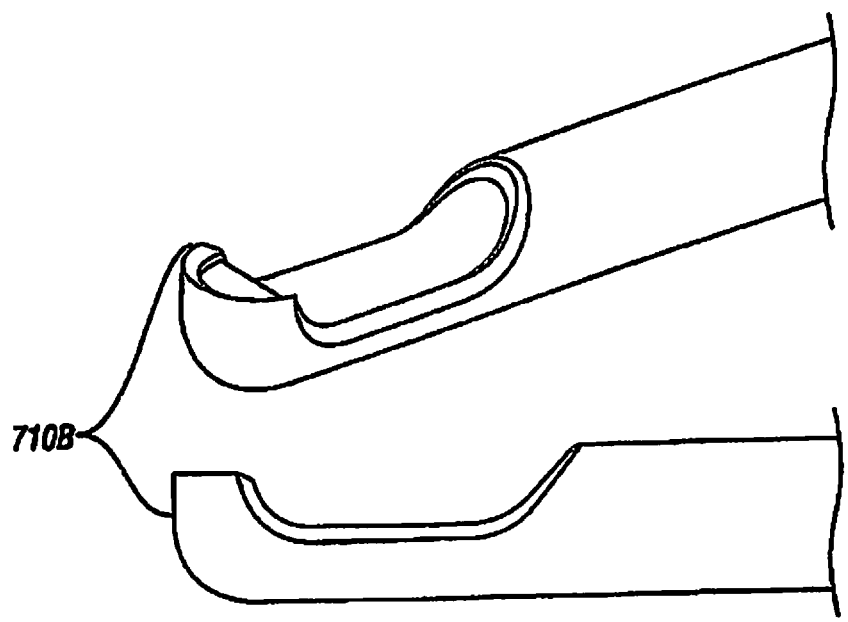
FIG. 7B shows a perspective view and a side view of a customized tip comprising a cup curette tip shaft.
Figure 7C:
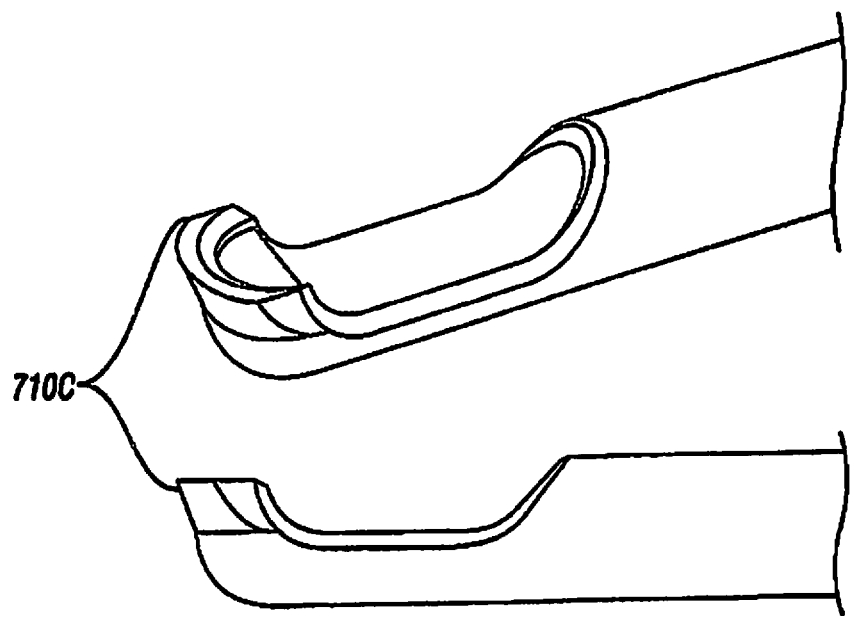
FIG. 7C shows a perspective view and a side view of a customized tip comprising a modified cup curette tip shaft.

FIGS. 7A-7C show a variety of different designs for customizable tips, according to another aspect of the present disclosure. Each of these customizable tips may function in the manner set forth above, or in other ways that will be readily understood by one of ordinary skill in the art. For example, FIG. 7A shows a serrated curette tip 710A which may be useful for gentle endplate scraping. FIG. 7B shows a cup curette tip 710B which may be useful for performing scraping via a pulling motion. FIG. 7C shows a modified cup curette tip 710C which may be useful for scraping via a pushing or pulling motion. It should be noted that it will be readily understood by one of ordinary skill in the art that the disclosure need not be so limited. The customizable tips set forth in the present disclosure may include any scraping instrument which may facilitate the severing of tissue by scraping.

Figure 8A:
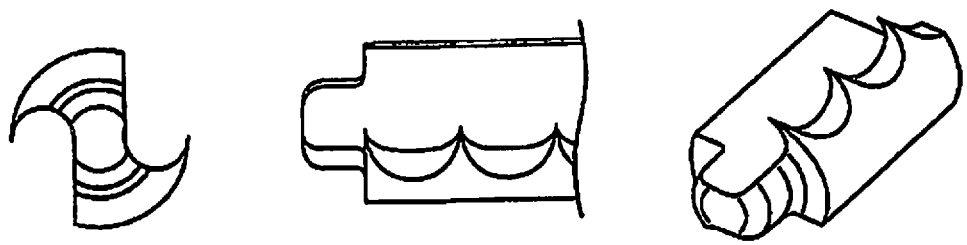
FIG. 8A shows a front view, a top view, and a perspective view of a customized cutter comprising a craw cutter.
Figure 8B:
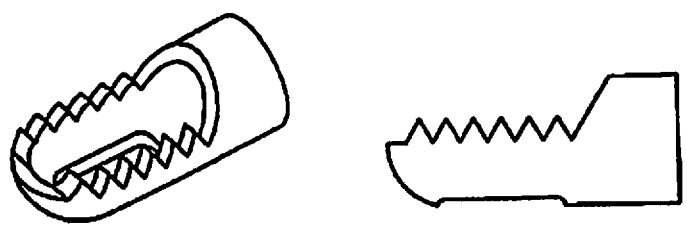
FIG. 8B shows perspective and side views of a customized cutter comprising a bullet tip serrated cutter.
Figure 8C:
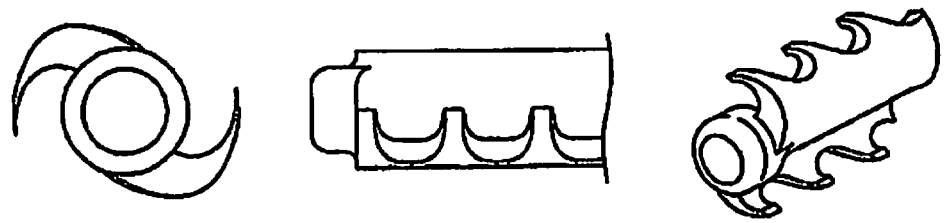
FIG. 8C shows a front view, a top view, and a perspective view of a customized tip comprising a tornado cutter.
Figure 8D:
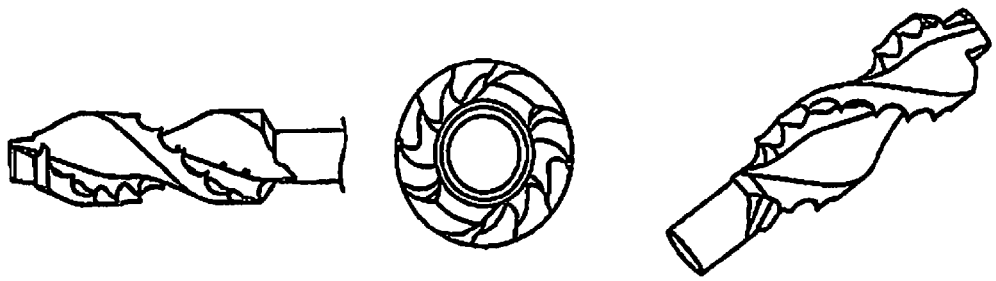
FIG. 8D shows a front view, a top view, and a perspective view of a customized cutter comprising a cyclone cutter.

According to another aspect of the present disclosure, FIGS. 8A-8D show a variety of different designs for cutting instruments which may be part of, or coupled to, for example, the threaded shaft 360 (shown in FIGS. 6A-6C). FIG. 8A shows various views of an example of a craw cutter; FIG. 8B shows various views of an example of a bullet tipped serrated cutter; FIG. 8C shows various views of an example of a tornado cutter; and FIG. 8D shows various views of an example of a cyclone cutter. It is noted that it will be readily understood by one of ordinary skill in the art that the disclosure need not be so limited. The customizable tips set forth in the present disclosure may include any cutting instrument which may facilitate the severing of tissue.

Figure 9:
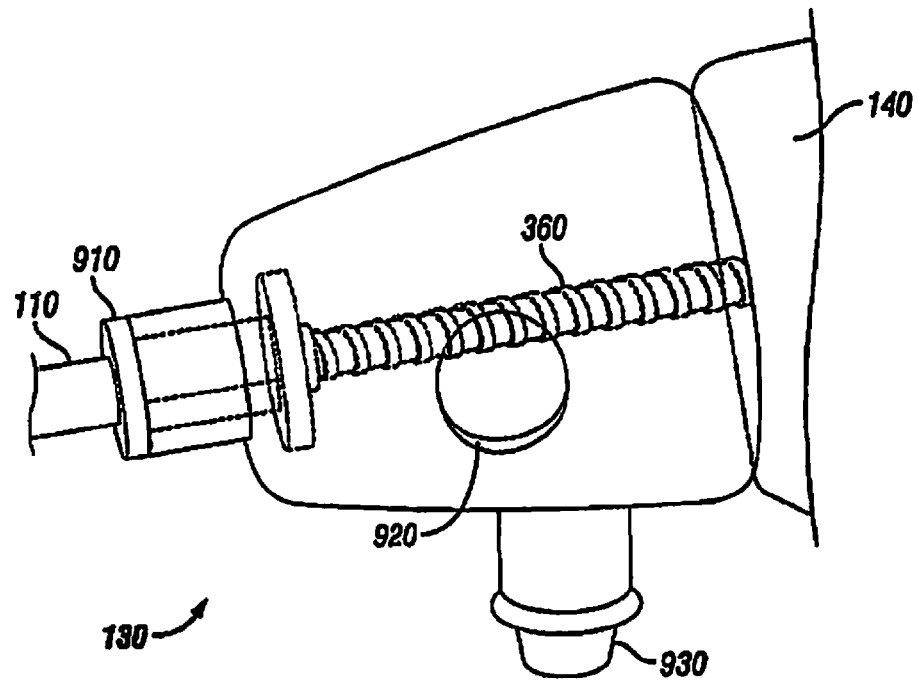
FIG. 9 shows a collection chamber that may be coupled to a tissue removal device, according to a further aspect of the present disclosure.

FIG. 9 shows an example of a collection chamber 130 according to an aspect of the present disclosure. The collection chamber 130 may include a connector 910, pluggable hole 920 and a pluggable port 930. The collection chamber 130 may include at least a partial enclosure that may be made of a transparent material in order to provide a surgeon with the ability to see through collection chamber 130. The material may include, but it is not limited to, e.g., plastic, glass, plexiglass, acrylic glass, etc. This provides a surgeon with the ability to inspect the contents of collection chamber 130 in order to verify the effectiveness of a procedure. It will be readily understood by one of ordinary skill in the art that collection chamber 130 of the present disclosure need not be so limited. The collection chamber 130 may be made of any material, e.g., transparent or non-transparent, that is capable of serving as at least a partial enclosure where tissue, severed by a tissue removal device 100, may be deposited with the aid of an auger-like suction mechanism.

Collection chamber 130 may include a connector 910. The connector 910 may be, for example, integrally formed as a single piece with the collection chamber 130, integrally formed as a single piece with the outer shaft 110, integrally formed as a single piece with the collection chamber 130 and the outer shaft 110, or provided as a separate component that may be attached to the collection chamber 130 and outer shaft 110. Connector 910 may include a pass-through opening to allow the threaded shaft 360 to extend through the connector 910 and into the outer shaft 110, with access to the collection chamber 130 in order to deposit tissue severed and removed by tissue removal device 100. As such connector may serve as a tunnel allowing threaded shaft 360 to extend from the surgical site, through outer shaft 110, and into the collection chamber 130.

Collection chamber 130 may include a pluggable hole 920. During operation of the tissue removal device 100, a plug (not shown) may be inserted into pluggable hole 920 in an attempt to create an enclosure which collects tissue that is severed and removed by the tissue removal device 100. However, after (or while) the procedure is performed, the plug may be removed from pluggable hole 920, thereby providing a surgeon with access to the sample residing in collection chamber 130. With the plug removed, a surgeon may then perform a biopsy of the collected tissue through pluggable hole 920.

Collection chamber 130 may include a pluggable port 930. When tissue removal using the disclosure's auger-like suction is being performed, pluggable port 930 may be sealed with a plug (not shown), where the auger-like suction is implemented without suction based on generated airflow. However, alternatively, or in combination, pluggable port 930 may be unsealed (i.e., unplugged) and coupled to a machine (such as, e.g., a vacuum, a pump, or the like) which generates airflow based suction. The collection chamber 130 provides the versatility for a surgeon to be able to supplement the auger-like suction used to remove severed tissue with a conventional surgical suction unit based on generated airflow. Coupling a conventional, surgical suction unit via pluggable port 930 may be particularly advantageous for surgeons who utilize, e.g., saline solution in the tissue removal process, wherein the conventional surgical suction unit may be used to remove, e.g., the saline solution.

FIG. 10 shows an example of a tissue removal system 1000, which includes power connections and the tissue removal device. In the tissue removal system 1000, the tissue removal device may be powered by a battery pack 1020 and include an on/off toggle switch 1010. The tissue removal system may include, e.g., a stepping motor, or any other driving mechanism that is capable of precise and quick response and control to drive or revolve the threaded shaft 360. Tissue removal system 1000 may also include a pedal 1030 which may be used to vary the speed with which the threaded shaft revolves. While an aspect of the disclosure provides that tissue removal device may be powered by a battery pack, it is noted that the tissue removal system 1000 may include other power supply means, including, e.g., electric power received from residential or commercial power supplies via, e.g., a power cord and plug 1040.

The disclosure provides numerous advantages over conventional devices. In light of the disclosure, there is no longer a need for costly capital equipment required to power a tissue removal device. Additionally, the disclosure may be disposable and come in sterile packaging allowing the disclosure to be used by surgeons who may not have access to all methods required for continuously sterilizing equipment. Additionally, the window cut (or formed) into the handle, allows a surgeon to see the height of a blade, thereby providing surgeons with confidence that they have expanded and/or contracted the blade to the correct height. And, the auger-like suction mechanism ensures that the suction mechanism will not clog and bind up the cutting shaft.

While the present disclosure has been described in terms of exemplary aspects, those skilled in the art will recognize that the present disclosure can be practiced with modifications in the spirit and scope of the appended claims. These examples given above are merely illustrative and are not meant to be an exhaustive list of all possible designs, aspects, applications or modifications of the present disclosure.

What is claimed is:

1. A method for removing tissue using a tissue removal device comprising an outer shaft, a threaded inner shaft extending through the outer shaft, a cutting portion extending from the threaded inner shaft, and a collection chamber connected to the outer shaft, the method comprising:
    accessing an area for tissue removal;
    cutting a portion of tissue at a surgical site with the cutting portion of the tissue removal device; and
    moving the cut portion of tissue away from the surgical site through the outer shaft and into the collection chamber using the threaded inner shaft, wherein the threaded inner shaft includes a plurality of sections with different threading to enhance transportation of the cut portion of tissue through the tissue removal device,
    wherein the threaded inner shaft includes at least three distinct threaded sections, including distal, intermediate and proximal sections, wherein the distal section comprises a helical cutting section, the helical cutting section in the distal section is adjacent to the intermediate section, and the intermediate section has sharper threads relative to the helical cutting section.

2. The method of claim 1, wherein the threaded inner shaft moves the cut portion of tissue through rotation of the threaded inner shaft.

3. The method of claim 2, wherein the cutting portion rotates at the same rotational velocity as the threaded inner shaft.

4. The method of claim 2, further comprising varying the speed at which the threaded inner shaft revolves.

5. The method of claim 1, wherein the outer shaft further comprises a shaft cutting tool, and the shaft cutting tool may further scrape the tissue at the surgical site, wherein the shaft cutting tool includes a serrated curette tip or a cup curette tip.

6. A method for removing tissue, the method comprising:
    accessing an area for tissue removal;
    providing a tissue removal device for removing tissue, the tissue removal device comprising:
        a cutting portion that is configured to remove a tissue sample from a surgical site;
        a collection chamber that receives the tissue sample; an outer shaft that is configured to convey and guide the tissue sample to the collection chamber; and
        an inner shaft that is configured to transport the tissue sample from the surgical site to the collection chamber;

a retriever attached to a distal end of the threaded shaft;
wherein the inner shaft includes at least three distinct threaded sections, including distal, intermediate and proximal sections, wherein the distal section comprises a helical cutting section,
wherein the helical cutting section in the distal section is adjacent to the intermediate section, wherein the intermediate section has sharper threads relative to the helical cutting section.

7. The method of claim 6, further comprising cutting a portion of tissue at the surgical site with the cutting portion of the tissue removal device.

8. The method of claim 7, further comprising moving the cut portion of tissue away from the surgical site through the outer shaft and into the collection chamber using the threaded inner shaft.

9. The method of claim 6, wherein the threaded inner shaft moves the cut portion of tissue through rotation of the threaded inner shaft, and the cutting portion rotates at the same rotational velocity as the threaded inner shaft.

10. The method of claim 6, wherein the cutting portion comprises a customizable tip.

11. The method of claim 10, wherein the customizable tip comprises a cutter or a flexible cutting blade.

12. The method of claim 6, wherein the intermediate section is adjacent to the proximal section, wherein the proximal section has flatter threads relative to the intermediate section.

13. A method for removing tissue, the method comprising:
accessing an area for tissue removal;
providing a tissue removal device for removing tissue, the tissue removal device comprising:
  a cutting portion that is configured to remove a tissue sample from a surgical site;
  a collection chamber that receives the tissue sample;
  an outer shaft that is configured to convey and guide the tissue sample to the collection chamber; and
  an inner shaft that is configured to transport the tissue sample from the surgical site to the collection chamber,
  wherein the inner shaft includes at least three distinct threaded sections, including distal, intermediate and proximal sections, wherein the distal section comprises a helical cutting section,
  wherein the helical cutting section in the distal section is adjacent to the intermediate section, wherein the intermediate section has sharper threads relative to the helical cutting section.

14. The method of claim 13, further comprising cutting a portion of tissue at the surgical site with the cutting portion of the tissue removal device; and moving the cut portion of tissue away from the surgical site through the outer shaft and into the collection chamber using the threaded inner shaft.

* * * * *